US008173114B2

(12) United States Patent
Suzuki et al.

(10) Patent No.: US 8,173,114 B2
(45) Date of Patent: May 8, 2012

(54) EXCRETION ACCELERATOR FOR ACCUMULATIVE CHLORINE COMPOUND

(75) Inventors: Kazuo Suzuki, Tokyo (JP); Shigekazu Nakajima, Tokyo (JP); Shinji Yano, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 546 days.

(21) Appl. No.: 10/432,871

(22) PCT Filed: Nov. 27, 2001

(86) PCT No.: PCT/JP01/10310
§ 371 (c)(1),
(2), (4) Date: Oct. 17, 2003

(87) PCT Pub. No.: WO02/43744
PCT Pub. Date: Jun. 6, 2002

(65) Prior Publication Data
US 2004/0047834 A1 Mar. 11, 2004

(30) Foreign Application Priority Data
Nov. 28, 2000 (JP) ................................. 2000-361834

(51) Int. Cl.
*A61K 31/74* (2006.01)
(52) U.S. Cl. ...................................................... 424/78.1
(58) Field of Classification Search .................. 424/489, 424/78.1
See application file for complete search history.

(56) References Cited

U.S. PATENT DOCUMENTS

| 4,777,042 A | 10/1988 | Toda et al. .................. 424/79 |
| 5,414,068 A | 5/1995 | Bliem et al. ................. 528/288 |
| 5,496,545 A * | 3/1996 | Holmes-Farley et al. . 424/78.11 |
| 5,521,214 A * | 5/1996 | Bryant et al. ................. 514/443 |
| 5,607,669 A | 3/1997 | Mandeville, III et al. . 424/78.12 |
| 5,840,339 A * | 11/1998 | Kunin ........................... 424/489 |
| 5,980,881 A * | 11/1999 | Mitsuka et al. .............. 424/78.1 |
| 6,562,860 B1 * | 5/2003 | Keller et al. ................. 514/431 |
| 6,733,780 B1 * | 5/2004 | Tyler et al. ................... 424/464 |

FOREIGN PATENT DOCUMENTS

| JP | 60-209523 | 10/1985 |
| JP | 07-206688 | 8/1995 |
| JP | 10-501842 | 2/1998 |

OTHER PUBLICATIONS

Iida, T et al: Fukuoka Igaku Zasshi. May, 1997 vol. 88(5) pp. 177-185.*
Iida, T et al: Fukuoka Igaku Zasshi, May 1997, vol. 88(5) pp. 186-192.*
Cohn et al. (Treatment of chlordecone (KEPONE) toxicity with cholestyramine: Results of a Controlled Clinical Trial, in New. Eng. J. of Medicine, vol. 298, pp. 243-248, 1978).*
Bhatnager ("Lipid Lowering Drugs in the management of Hyperlipidaemia" in Pharmacol. Ther. vol. 79, No. 3, pp. 205-230, 1998).*
Ellen et al. (in Environmental and Occupational Medicine, Third edition, William N. Rom edited, 1998, chapter 85, pp. 1185-1198).*
Honda et al. ("Studies on adsorption characteristics of bile acids and methotrexate to a new type of anion-exchange resin, colestimide," in Chem. Pharm. Bull. (Tokyo), Jul. 2000, vol. 48, No. 7, pp. 978-981, English abstract).*
Lida et al. "Recent trend of polychlorinated dibenzo-p-dioxins and their related compounds in the blood and sebum of Yusho and Yu-Cheng patients," in Chemosphere, vol. 38, Issue 5, Feb. 1999, pp. 981-993.*
Database Biosis, Biosciences Information Service, D. Polin et al., "Enhanced Withdrawal of Polychlorinated Biphenyls a Comparison Colestipol Mineral Oil Propylene Glycol and Petroleum Jelly With or Without Restricted Feeding", XP002332360, Database Accession No. PREV198988090865 * Abstract*, & Poultry Science, vol. 68, No. 7, 1989, pp. 885-890.
William J. Cohn et al., "Treatment of Chlordedone (kepone) Toxicity with Cholestyramine", N. Engl. J. Med., vol. 298, (1978), pp. 243-248.
Kunimasa Morita et al., "Stimulating Effect of Dietary Fiber on Fecal Excretion of Polychlorinate Dibenzofurans (PCDF) and Polychlorinated dibenzo-p-dioxins (PCDD) in Rats", Fukuoka Igaku Zasshi, vol. 84, No. 5, (1993), pp. 317-325.
Burke Steven et al., "Sevelamer Hydrochloride (Renagel (R)), a Nonabsorbed Phosphate-Binding Polymer, does not Interfere with Digoxin or Warfarin Pharmacokinetics", Journal of Clinical Pharmacology, vol. 41, No. 2, Feb. 2001, pp. 193-198.
Abstract of: Kunimasa Morita et al., "Stimulating Effect of Dietary Fiber on Fecal Excretion of Polychlorinated Dibenzofurans (PCDF) and Polychlorinated dibenzo-p-dioxins (PCDD) in Rats", Fukuoka Igaku Zasshi, vol. 84, No. 5, (1993), pp. 273-281.
"Seikagakujiten", Oct. 8, 1998, p. 821, Item of "Daiokishin" (in Japanese Language).

\* cited by examiner

*Primary Examiner* — Blessing Fubara
(74) *Attorney, Agent, or Firm* — Wenderoth, Lind & Ponack, L.L.P.

(57) ABSTRACT

An agent for promoting excretion of an accumulative chlorine compound comprising a pharmaceutically acceptable anion exchange resin, which is a novel agent that is for promoting the excretion of an accumulative chlorine compound and is capable of efficiently excreting residual chlorinated compounds including dioxins as typical examples.

13 Claims, No Drawings

EXCRETION ACCELERATOR FOR ACCUMULATIVE CHLORINE COMPOUND

This application is a U.S. national stage of International Application No. PCT/JP01/10310 filed Nov. 27, 2001.

FIELD OF THE INVENTION

The present invention relates to an agent for promoting excretion of accumulative chlorine-containing compounds, which comprises a pharmaceutically acceptable anion exchange resin.

BACKGROUND OF THE INVENTION

Chlorine compounds which readily remain in vivo, specifically, an accumulative chlorine-containing compound including dioxins as typical examples, have carcinogenesis and likely cause liver disorder and the like, and the compounds are transferred from a gravida to a fetus. Accordingly, effects of the compounds on a human body have been focused, and recently considered as severe problems. It is considered that approximately 90% of uptake of the accumulative chlorine-containing compounds taken into a human body comes from food, and accumulative chlorine-containing compounds after the uptake are accumulated in fatty tissues. Therefore, it is desired to provide an agent for promoting excretion of accumulative chlorine-containing compounds, which can excrete accumulative chlorine-containing compounds after being uptaken in vivo as efficiently as possible.

Some trials wherein cholestyramine (trade name: Questran, Bristol-Myers Squibb Company), which is an anion exchange resin and is sold as a cholesterol depressant, was used as an agent for promoting excretion of dioxins, are described in Fukuoka Acta Med. 78(5): 266-280, 1987; Fukuoka Acta Med. 78(5): 249-253, 1987; Fukuoka Acta Med. 82(5): 326-329, 1991; Fukuoka Acta Med. 82(5): 310-316, 1991; Fukuoka Acta Med. 82(5): 305-309, 1991; Xenobiotica, Vol. 21, No. 3, 351-357, 1991; Fukuoka Acta Med. 82(5): 330-334, 1991; Fukuoka Acta Med. 82(5): 317-325, 1991; Fukuoka Acta Med. 84(5): 257-262, 1993; Fukuoka Acta Med. 84(5): 282-286, 1993; Fukuoka Acta Med. 86(5): 226-233, 1995; Fukuoka Acta Med. 88(5): 186-192, 1997 and the like. However, effectiveness of the resin remains unclear at present, because these articles relate to a trial wherein cholestyramine alone was effective, a trial wherein cholestyramine alone was ineffective, and a trial wherein a combined use of cholestyramine with rice bran fiber was effective and the like.

Accordingly, an objective of the present invention is to provide an agent for promoting excretion of accumulative chlorine-containing compounds, which comprises as an active ingredient a pharmaceutically acceptable anion exchange resin.

DISCLOSURE OF THE INVENTION

The inventors of the present invention conducted various researches to achieve the foregoing object. As a result, they found that a pharmaceutically acceptable anion exchange resin alone as an active ingredient, including colestimide (2-methylimidazol-epichlorohydrin copolymer) known as a cholesterol lowering agent, has an action of promoting excretion of accumulative chlorine-containing compounds as represented by dioxins.

Thus the gist of the present invention relates to an agent for promoting excretion of an accumulative chlorine-containing compound, which comprises as an active ingredient a pharmaceutically acceptable anion exchange resin.

According to preferred embodiments of the present invention, there are provided the above agent for promoting excretion of an accumulative chlorine-containing compound, characterized in that the pharmaceutically acceptable anion exchange resin has an action of adsorbing an accumulative chlorine-containing compound labeled with a radioactive compound in Solution 2 defined in the Japanese Pharmacopoeia; the above agent for promoting excretion of an accumulative chlorine-containing compound, characterized in that the pharmaceutically acceptable anion exchange resin is selected from colestimide, cholestyramine resin, colestipol, colesevelam hydrochloride, and sevelamer hydrochloride; the above agent for promoting excretion of an accumulative chlorine-containing compound, characterized in that the pharmaceutically acceptable anion exchange resin is selected from colestimide, colestipol, colesevelam hydrochloride, and sevelamer hydrochloride; the above agent for promoting excretion of an accumulative chlorine-containing compound, characterized in that the pharmaceutically acceptable anion exchange resin is synthesized by polymerization reaction of an epichlorohydrin derivative with an amine; the above agent for promoting excretion of an accumulative chlorine-containing compound, characterized in that the pharmaceutically acceptable anion exchange resin is colestimide; the above agent for promoting excretion of an accumulative chlorine-containing compound, characterized in that the accumulative chlorine-containing compound is a dioxin; the above agent for promoting excretion of an accumulative chlorine-containing compound, characterized in that the dioxin has a chemical structure as represented by the following general formula (I) or (II) wherein 1 to 8 chlorine atoms are substituted at positions 1 to 9;

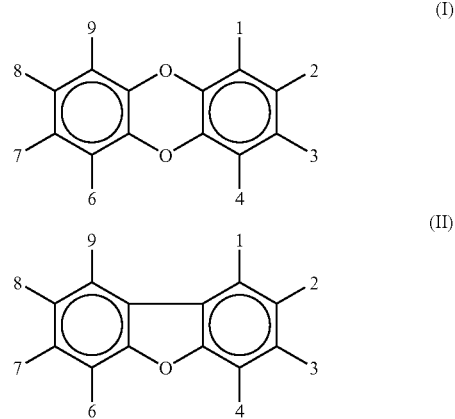

the above agent for promoting excretion of an accumulative chlorine-containing compound, characterized in that the dioxin has a chemical structure as represented by the above general formula (I) or (II) wherein chlorine atoms are substituted at positions 2, 3, 7 and 8; and the above agent for promoting excretion of an accumulative chlorine-containing compound, characterized in that the dioxin is tetrachlorodibenzodioxin.

Other gists of the present invention relates to a pharmaceutical composition for promoting excretion of an accumulative chlorine-containing compound, which comprises as an active ingredient a pharmaceutically acceptable anion exchange resin; a medicament for therapeutic treatment of a disease selected from toxicosis by chlorine compounds and "yusho", which comprises as an active ingredient a pharmaceutically acceptable anion exchange resin; and a method for promoting excretion of an accumulative chlorine-containing compound by using a pharmaceutically acceptable anion exchange resin as an active ingredient.

BEST MODE FOR CARRYING OUT THE INVENTION

The present invention will be further explained in detail.

According to the present invention, a pharmaceutically acceptable anion exchange resin is an anion exchange resin that can be administered as a medicament, and is not particularly limited so long as the resin has an action of promoting the excretion of an accumulative chlorine-containing compound including dioxins as typical examples. Preferably, as shown in the following Examples, the anion exchange resin preferably has an action of adsorbing an accumulative chlorine-containing compound labeled with a radioactive atom in Solution 2 in the Japanese Pharmacopoeia. A most preferred example of such class of anion exchange resin is colestimide (2-methylimidazol-epichlorohydrin copolymer). Colestimide has an irregularly assembled and complicated stereostructure, and is represented by the fundamental structure of the following formula (III) that is partially represented by the following formula (IV). The resin is obtained by polymerization reaction of an epichlorohydrin derivative with an amine including an imidazole derivative as a typical example, specifically, by the manufacturing method described in JP Patent Publication (Kokai) No. 60-209523.

Examples of other preferable anion exchange resins include the above cholestyramine resin, and colestipol (N-(2-aminoethyl)-N'-[2-[(2-amino-ethyl)-amino]ethyl]-1, 2-ethanediamine polymer synthesized by addition of (chloromethyl)oxirane), which are sold by SIGMA. In addition, the cholestyramine resin is a strongly basic anion exchange resin including styrene-divinylbenzene copolymer which contains quarternary ammonium groups, and its fundamental structure is represented by the following formula (V).

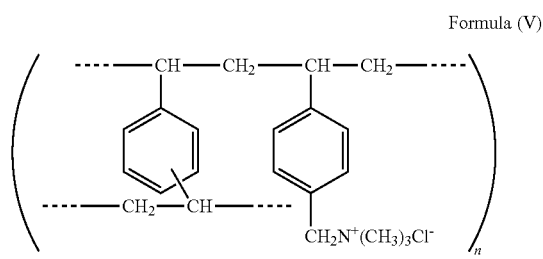

Formula (V)

Further, the fundamental structure of colesevelam hydrochloride is represented by the following formula (VI). The resin can be produced by the method of U.S. Pat. No. 5,607,669, or any method similar thereto.

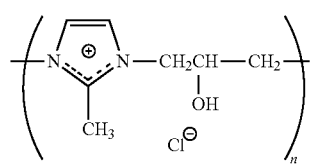

(III)

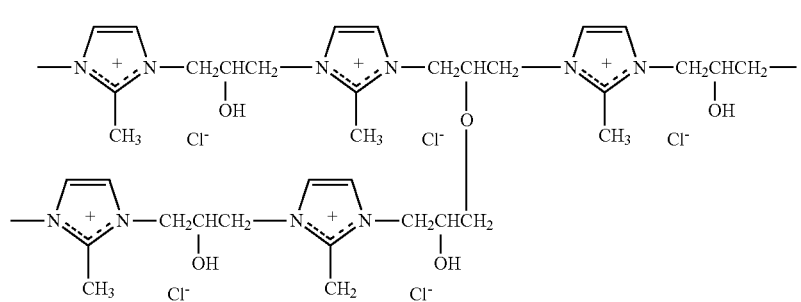

(IV)

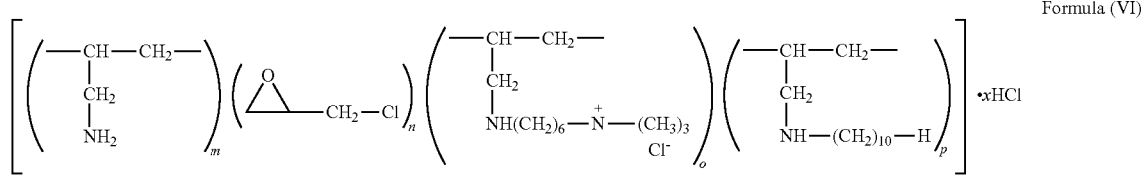

Formula (VI)

The fundamental structure of sevelamer hydrochloride is represented by the following formula (VII), and sevelamer hydrochloride can be produced by the method of U.S. Pat. No. 5,496,545, or any method similar thereto.

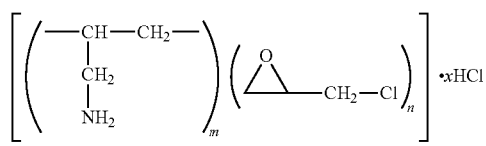

Formula (VII)

In addition, other anion exchange resins as described in Japanese Patent Publication of International Application (Kohyo) Nos. 9-504782, 9-500368, 10-501264, 10-501842, 11-507093, 11-512074, and 5-512332, and Japanese Patent Unexamined Publication (Kokai) Nos. 8-208750, 9-202732, 10-114661, and 11-228449 can also be used in the present invention, as long as they do not beyond the gist of the present invention.

The above compound an active ingredient, per se, can be used as the agent for promoting excretion of accumulative chlorine-containing compounds of the present invention. It is preferred that a pharmaceutical composition containing the above active ingredient is manufactured by using an widely-used additive for pharmaceutical preparation, and then use the same.

Examples of the pharmaceutical composition include tablets, capsules, subtle granules, pills, troches, and liquids, and these are orally administered.

The pharmaceutical composition for oral administration can be manufactured by a conventional method widely used, such as mixing, filling or compressing. Further, by applying repeated formulation procedures, the active ingredient may be distributed in a pharmaceutical composition containing a large amount of excipient. For example, tablets or capsules used for oral administration are preferably provided as unit dosage forms, and they may contain ordinarily used carriers for pharmaceutical preparation, such as a binder, excipient, diluent, compressing agent, lubricant, disintegrator, coloring agent, flavoring agent, and moistening agent. A tablet may be manufactured as a coated tablet according to a well known method in the art by using a coating agent, for example.

Examples of a preferable excipient include cellulose, mannitol, and lactose. Starch, polyvinylpyrrolidone, starch derivative including sodium starch glycolate or the like as a disintegrator, and sodium lauryl sulfate or the like as a lubricant can be used as additives for the pharmaceutical preparation. Orally-available pharmaceutical compositions in the form of a liquid are provided as, for example, a pharmaceutical composition, such as an aqueous or oil suspension, a solution, an emulsion, a syrup, or an elixir; or a dry pharmaceutical composition which can be re-dissolved in water or an appropriate medium before use.

In the liquids, commonly used additives may be added such as, for example, a precipitation preventing agent, such as sorbitol, syrup, methyl cellulose, gelatin, hydroxyethylcellulose, carboxymethylcellulose, aluminum stearate gel, or hydrogenated edible fat; an emulsifier such as lecithin, sorbitan monooleate, or gum arabicum; oily esters such as almond oil, refined coconut oil, or glycerin esters; a non-aqueous medium such as propylene glycol, or ethyl alcohol (edible oils may be included); a preservative such as methylester, ethyl ester, or propyl ester of p-hydroxybenzoic acid, or sorbic acid; and an optionally ordinarily used flavoring agent or coloring agent.

The above pharmaceutical composition for oral administration such as in the forms of tablets, capsules, or subtilized granules generally contain 5 to 95% by weight, preferably 25 to 90% by weight of the active ingredient.

The colestimide has been sold by Mitsubishi Pharma Corporation as a trade name of "Cholebine", and Cholebine may be used, per se, for the present invention.

The accumulative chlorine-containing compound according to the present invention is not specifically limited, so long as the compound is a chlorinated compound that readily remains in vivo, and its excretion is promoted by the above-defined anion exchange resin. Typical examples include a class of dioxins. The dioxins has a chemical structure as represented by the above formula (I) or (II) wherein 1 to 8 chlorine atoms are substituted at positions 1 to 9. Among these compounds, preferred are those represented by the above general formula (I) or (II) wherein chlorine atoms are substituted at positions 2, 3, 7 and 8. Most preferably, the compound is tetrachlorodibenzodioxin.

The agent for promoting excretion of an accumulative chlorine-containing compound of the present invention is particularly effective for treatment of toxicosis caused by chlorinated compounds and "yusho (oil poisoning sympton)".

Dose of the agent for promoting excretion of an accumulative chlorine-containing compound of the present invention may appropriately be determined depending on the age, health conditions, and body weight of a patient, and the severity of a disease, the type of and frequency of therapy or treatment being simultaneously applied, the nature of desired effects and the like. In general, a daily dose for an adult may be 1 to 60 g as a weight of the active ingredient, and the agent may be administered once or several times a day.

EXAMPLE

The present invention will be specifically explained by referring to the examples. However, the present invention is not limited to these examples. The colestimide used below was produced by the preparation method described in Japanese Patent Unexamined Publication (Kokai) No. 60-209523.

Example 1

(Preparation of Intestinal Juice Containing $^{14}$C-labeled Tetrachlorodibenzodioxin)

Sodium cholate and oleic acid were weighed and placed in a glass container in an amount equivalent to 10 mmol and 20 mmol, respectively, and dissolved in a small amount of chloroform. A toluene solution of $^{14}$C-labeled tetrachlorodibenzodioxin (hereinafter also referred to as $^{14}$C-TCDD) was added in an amount equivalent to 40,000 to 50,000 dpm, and then the solution was stirred and mixed. Then, the solvent was removed by evaporation under nitrogen flow (under warming at approximately 40° C.). 20 mL of Solution 2 of the Japanese Pharmacopoeia was added to the residue, followed by ultrasonication for approximately 1 minute to obtain $^{14}$C-TCDD-containing intestinal juice.

(Addition of Test Substance and Preparation of Sample to be Measured)

Solution 2 of the Japanese Pharmacopoeia was prepared by mixing 0.2 mol/L potassium dihydrogen phosphate aqueous solution, 0.2 mol/L sodium hydroxide aqueous solution, and purified water at a ratio of 250/118/632 (pH=6.8). 3, 10, and 30 mg (each n=3) of colestimide were weighed and placed into PP tubes, and each 1 mL of the above $^{14}$C-TCDD-containing intestinal juice was added. Further, control sample was prepared from only the $^{14}$C-TCDD-containing intestinal juice.

The tubes were each stoppered tightly, agitated with a vortex mixer, and then incubated at 37° C. for 10 minutes. Centrifugation was performed (3,000 rpm/min for 5 minutes), and then the supernatant (0.5 mL each) was collected in a counting vial to obtain a sample for radioactivity measurement. (Radioactivity measurement) 5 mL of a scintillation cocktail (Clear-sol, nacalai tesque) was added to each sample and the resulting mixtures were prepared for radioactivity measurement, and then measurements were carried out by using a liquid scintillation counter (TRI-CARB 2300TR, PACKARD) in which quenching correction was performed by the tSIE method (transformed Special Index of External standard). The measurement was performed once per vial for 5 minutes. A net count value was obtained by subtracting background data, which were obtained by measuring only the scintillation cocktail once for 10 minutes, from the measured value.

(Calculation of Binding Rate)

From the result of the above radioactivity measurement (the mean value of n=3), a binding rate of $^{14}$C-TCDD to each test substance was calculated by using the following equation.

Binding rate (%)=(radioactivity in the filtrate when the test substance was added)/(radioactivity in the control filtrate)×100

(Result)

The results of measurements of the binding rates of $^{14}$C-TCDD to colestimide in the artificial intestinal juice are shown in the table below.

| Test Compound | Amount added | Radioactivity in supernatant Experimental value | Average | Binding rate of TCDD (%) |
|---|---|---|---|---|
| | — | 3399.1<br>3509.8<br>3492.6 | 3467.2 | — |
| Colestimide | 3 | 1828.7<br>1948.9<br>1715.1 | 1830.9 | 47.2 |
| | 10 | 1177.0<br>1146.5<br>1259.0 | 1194.2 | 65.6 |
| | 30 | 334.1<br>233.1<br>305.8 | 291.0 | 91.6 |

As shown in the above results, it can be understood that colestimide adsorbs TCDD in a dose-depending manner, which is an accumulative chlorine-containing compound,.

INDUSTRIAL APPLICABILITY

According to the present invention, a novel agent for promoting excretion of an accumulative chlorine-containing compound is successfully provided, which is capable of efficiently excreting accumulative chlorine-containing compounds uptaken in vivo.

The present application was filed based on Japanese Patent Application No. 2000-361834 on which priority is claimed.

What is claimed is:

1. The method for promoting excretion of an accumulated dioxin in a human patient in need thereof, said method consisting essentially of administering colestimide as the sole active ingredient to the human patient in need thereof.

2. The method for promoting excretion of an accumulated dioxin in a human patient in need thereof, said method comprising administering colestimide as the sole active ingredient to the human patient in need thereof, wherein the colestimide is excreted with the accumulated dioxin.

3. The method for promoting excretion of an accumulative dioxin in a human patient in need thereof, said method comprising administering colestimide as the sole active ingredient to the human patient in need thereof, wherein the colestimide absorbs the accumulated dioxin, and the colestimide is excreted with the accumulated dioxin.

4. The method for promoting excretion of an accumulative in a human patient in need thereof, said method comprising administering colestimide as the sole active ingredient to the human patient in need thereof, wherein the colestimide is excreted with the accumulated dioxin.

5. A method for absorbing an accumulated dioxin in a human patient in need thereof, said method consisting essentially of administering colestimide as an active ingredient to the human patient in need thereof, wherein the colestimide absorbs the accumulated dioxin.

6. The method according to any one of claims 1-5, wherein the human patient is on with yusho or toxicosis caused by a dioxin.

7. The method according to any one of claims 1-5, wherein the human patient is on with yusho.

8. The method according to any one of claims 1-5, wherein the human patient is one with toxicosis caused by a dioxin.

9. The method according to any one of claims 1-5, wherein the dioxin has a chemical structure as represented by the following formula (I) or (II):

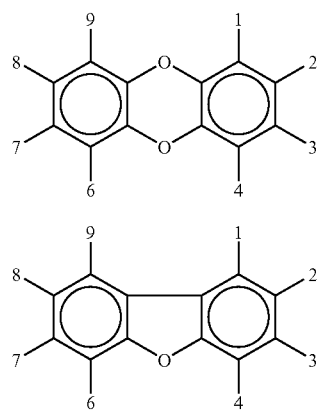

(I)

(II)

wherein 1 to 8 chlorine atoms are substituted at any of positions 1 to 4 and 6 to 9.

10. The method according to claim 9, wherein the dioxin has a chemical structure as represented by the formula (I) or (II) wherein chlorine atoms are substituted at positions 2, 3, 7, and 8.

11. The method according to claim 10, wherein the dioxin has a chemical structure as represented by the formula (I) wherein chlorine atoms are substituted at positions 2, 3, 7, and 8.

12. The method according to claim 10, wherein the dioxin has a chemical structure as represented by the formula (II) wherein chlorine atoms are substituted at positions 2, 3, 7, and 8.

13. The method according to any of claims 1-5, wherein the dioxin is tetrachlorodibenzodioxin.

* * * * *